United States Patent [19]
O'Lenick, Jr.

[11] Patent Number: 6,114,561
[45] Date of Patent: Sep. 5, 2000

[54] SILICONE SUNSCREENING ESTERS

[76] Inventor: Anthony J. O'Lenick, Jr., 2170 Luke Edwards Rd., Dacula, Ga. 30019

[21] Appl. No.: 09/452,435

[22] Filed: Dec. 2, 1999

Related U.S. Application Data

[63] Continuation-in-part of application No. 09/384,989, Aug. 30, 1999, which is a continuation-in-part of application No. 09/215,806, Dec. 18, 1998, Pat. No. 6,004,542, which is a continuation-in-part of application No. 09/040,431, Mar. 18, 1998, Pat. No. 5,908,949, which is a continuation-in-part of application No. 09/039,435, Mar. 16, 1998, Pat. No. 5,883,279.

[51] Int. Cl.$^7$ ............................................. C07F 7/08
[52] U.S. Cl. ............................................ 556/439; 556/428
[58] Field of Search ...................................... 556/439, 428

[56] References Cited

U.S. PATENT DOCUMENTS 3,511,699  5/1970  Sterman .
5,475,126  12/1995  Yoshida et al. ........................ 556/439

*Primary Examiner*—Paul F. Shaver

[57] ABSTRACT

The invention discloses novel sunscreening ester made by reacting (a) a carboxy silicone, and (b) the hydroxyl group of a sun screening agent. The compounds of the invention by virtue of (i) the silicone group, (ii) the sun screen group present in the compound are extremely efficient skin care compounds used in topical treatment of skin.

11 Claims, No Drawings

SILICONE SUNSCREENING ESTERS

RELATED APPLICATIONS

This application is a continuation in part of co-pending application Ser. No. 09/384,989, filed Aug. 30, 1999, which is in turn a continuation in part of Ser. No. 09/215,806 filed Dec. 18, 1998, now U.S. Pat. No. 6,004,542, which is in turn a continuation in part of Ser. No. 09/040,431 filed Mar.18, 1998, now U.S. Pat. No. 5,908,949 issued Jun. 1, 1999, which is in turn a continuation in part of application Ser. No. 09/039,435 filed Mar.16, 1998, now U.S. Pat. No. 5,883,279 issued Mar. 16, 1999.

THE INVENTION

The invention discloses novel sunscreening esters of silicone compounds which an ester linkage, and a silicone polymer. Compounds of the invention are made by reacting (a) a carboxy silicone, and (b) the hydroxyl group in a sunscreening compound selected from the group consisting of benzophenone 1, 3, 4, 6, 8, 10 and 12 to form an ester.

Compounds of the invention by virtue of (i) the silicone group, (ii) the ester group and (iii) the ultra violet absorbing group sunscreening group, the compounds are effective durable ultra-violet absorbers. We have surprisingly found that the reaction with the aromatic hydroxyl group of the sunscreening agent provides a most persistent material on the substrate and does not effect performance of the Ultra violet absorber. Substrate includes hair and skin, textile fabrics, carpets, paints and other materials to which materials that suffer from ultra violet degradation may be applied. An additional important aspect of the current invention is the fact that the compounds of the current invention having a molecular weight of over 1,500 do not penetrate the skin and are consequently non-irritating and do not contribute to skin sensitization.

The reaction used to prepare the compounds of the present invention is an esterification of a carboxy silicone and the aromatic group on the sunscreening agent. The resulting ester provides ultra violet absorbance and is durable to substrates like textile fabrics, hair and skin.

ARTS AND PRACTICES

Silicone compounds have been known to be active at the surface of plastic, cellulosic and synthetic fibers as well as paper. They are good nondurable lubricants and are very stable to oxidation, however, their high cost and lack of efficiency at low concentrations as well as low durability have made their acceptance in commercial products quite low. In all instances, commercially available quaternaries are the active ingredient in traditional laundry care markets, with little or no silicone added.

Placing sunscreening agents into silicone oil has several problems. Firstly, the sunscreening agents are insoluble in silicone fluids. This makes using these silicone compounds as delivery vehicles impossible. Secondly, silicone oil has low efficiency and low durability due to the fact that it is very water insoluble and deposits on the surface to obtain a minimum free energy in the solution. Simply, the silicone oil delivery to the surface by hydrophobic binding, not chemical bonding. At the surface, the dimethylpolysiloxane is a very effective fiber lubricant, however, there are two drawbacks, first; the dimethylpolysiloxane is not chemically bonded so the effect is very transient and disappears with one washing, and second; since there is no reaction of the dimethylpolysiloxane to the surface an equilibrium between fiber absorbed dimethylpolysiloxane and dimethylpolysiloxane in the dispersion results in very inefficient percentage of silicone deposited. A large amount of the expensive silicone goes down the drain with the waste water.

Silicone oils do not provide ultra violet absorption, and consequently protection from the damaging effects of the sun. The aromatic compounds that provide this type of absorbance are not durable to the surfaces of substrates.

U.S. Pat. No. 3,511,699 to Sterman issued May 12, 1970 teaches that epoxy compounds placed in the silicone backbone by hydrosilylation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds the efficiency and durability of the were not good enough to allow for cost effective incorporation of these materials in detergent formulations. This type of chemistry is not applicable to sunscreening compounds, for two reasons. First, the sunscreening agent is not soluble in this type of silicone compound either, and no reaction occurs with the sunscreening agent. Only with the reaction of the sun screening agent into the molecule with the proper silicone compound is the solubility, durability, and efficiency of ultra violet absorptivity achieved.

OBJECT OF THE INVENTION

It is the object of the present invention to provide a durable ultra violet protection to substrates like skin, hair and textile fabrics and fibers, as well as rubber and plastics. The presence of silicone in the molecule gives superior durability to these substrates, the presence of the sunscreening group gives superior ultra violet protection and the introduction of the ester linkage between the silicone and aromatic group results in a linkage which will biodegrade rapidly in waste water, making the compound less persistent in the waste water stream.

The formation of the ester linkage and the incorporation of the sunscreening group into the silicone of the present invention is accomplished by an esterification reaction of a carboxy silicone and the hydroxyl group of the sunscreening agent. That hydroxyl group is on an aromatic ring, that is it is a phenolic hydroxyl. This type of group reacts very efficiently with the carboxylic group of the silicone compound to provide efficient ultra violet absorbing molecules.

SUMMARY OF THE INVENTION

The compounds of this invention are made by the esterification of a carboxy silicone compound and sunscreening agent. Only if the compounds are specifically selected will compounds useful in the preparation of the compounds of the present invention be obtained.

Specifically, the compounds of the present invention are esters compounds which is prepared by the esterification reaction of;

(a) a silicone carboxylate conforming to the following structure:

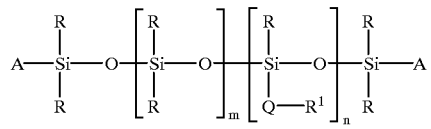

wherein:

R is methyl;

$R^1$ is H;

Q is a —$(CH_2)_c$—C(O)—O—;

c is an integer ranging from 3 to 17;

A is selected from —R or —Q—$R^1$, m is an integer ranging from 1 to 200;

n is an integer ranging 0 to 10 when A is —Q—R¹, and an integer ranging from 1 to 10 when A is R; and (b) a sunscreening compound selected from the group consisting of benzophenone 1, 3, 4, 6, 8,10 and 12.

The benzophenone compounds all have the required phenolic hydroxyl group. In some instances, there are two phenolic groups present. If both are reacted a polyester forms. Polyester products are acceptable, but more commonly only one of the groups is reacted, providing a preferred product.

Sunscreening Agents

Sunscreening agents useful in the synthesis of compounds of the present invention are known commercially available materials. They are made by several companies, most notably BASF. They are all listed in the Merck Index volume 12.

Benzophenone 1 is 2,4-dihydroxy-phenyl methanone. It conforms to the following structure;

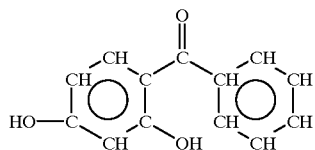

Benzophenone 3 is 2-hydroxy-4-methoxy benzophenone. It conforms to the following structure:

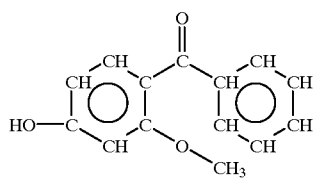

Benzophenone 4 is 5-benzoyl-4-hydroxy-2methoxybenzene sulfonic acid. It conforms to the following structure:

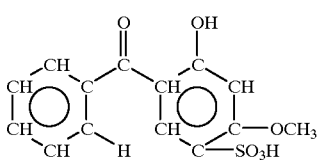

Benzophenone 6 is bis(2-hydroxy-4-methoxyphenyl) methanone. It conforms to the following structure:

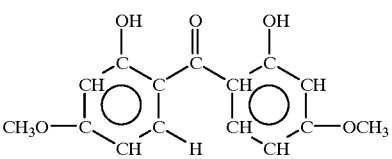

Benzophenone 8 is (2-hydroxy-4-methoxyphenyl) (2-hydroxyphenyl) methanone. It confirms to the following structure:

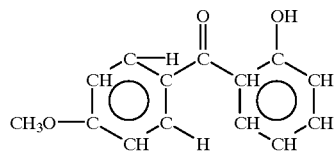

Benzophenone 10 is (2-hydroxy-4-methoxyphenyl)-(4-methyl-phenyl) methanone. It conforms to the following structure:

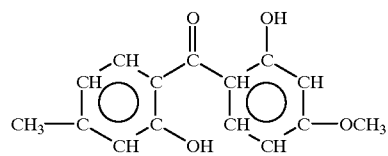

Benzophenone 12 is [2-hydroxy-4-(octyloxy)phenyl]-phenyl methanone. It conforms to the following structure:

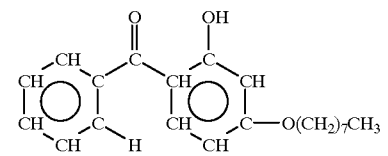

Compounds of the present invention conform to the following structure:

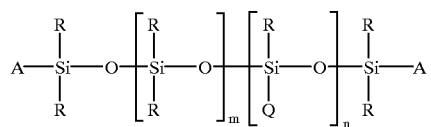

wherein:

R is methyl;

Q is a —(CH$_2$)$_c$—C(O)—O—R²;

c is an integer ranging from 3 to 17;

A is selected from —R or —Q m is an integer ranging from 1 to 200;

n is an integer ranging 0 to 10 when A is —Q, and an integer ranging from 1 to 10 when A is R:

R² is selected from the group consisting of

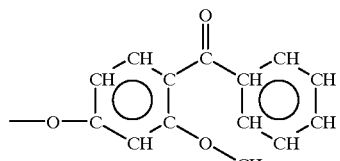

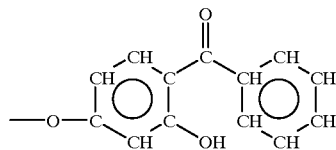

-continued
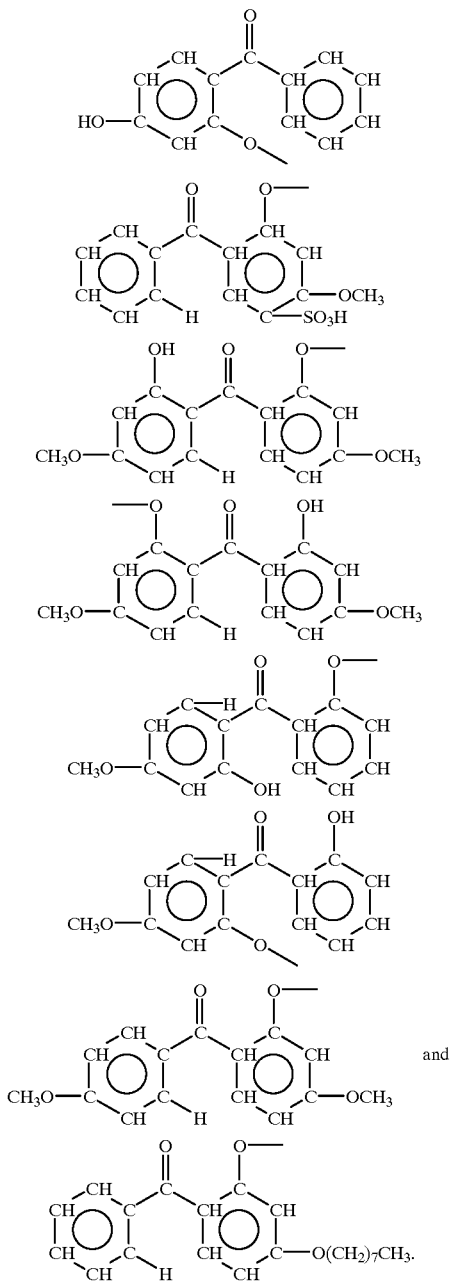
PREFERRED EMBODIMENTS
In a preferred embodiment $R^2$ is
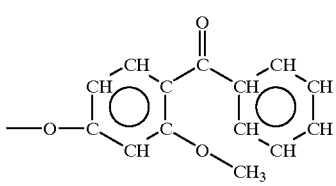
In another preferred embodiment $R^2$ is
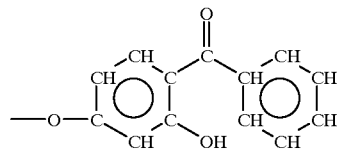
In another preferred embodiment $R^2$ is
In another preferred embodiment $R^2$ is
In a preferred embodiment $R^2$ is
In a preferred embodiment $R^2$ is
In a preferred embodiment $R^2$ is In a preferred embodiment $R^2$ is

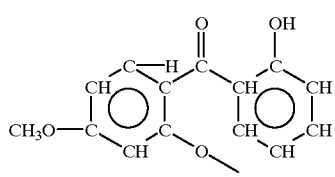

In a preferred embodiment $R^2$ is

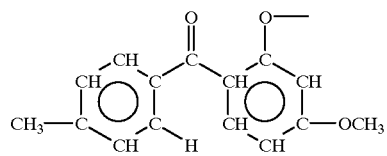

In a preferred embodiment $R^2$ is

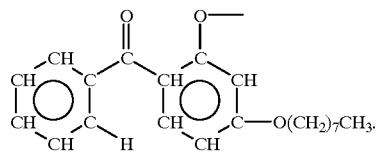

EXAMPLES

The compounds of the present invention are prepared by the reaction of a carboxy silicone compound and a sunscreening agent. Examples of suitable reactants are as follows:

All percentages given are based upon percent by weight, based upon the total weight of the entire batch. All temperatures are degrees C.

Reactants

Sunscreening Agents

Benzophenone 1
Benzophenone 3
Benzophenone 4
Benzophenone 6
Benzophenone 8
Benzophenone 10
Benzophenone 12

Carboxy Functional Silicone Compounds

Many manufacturers offer a series of carboxy functional silicone compounds suitable for use as raw materials in the preparation of the esters of the present invention. These materials are marketed under the many trade names. Siltech Inc. and Dow Corning.

The preferred method of placing this type of reactive carboxy group into the silicone polymer is by the reaction of silanic hydrogen containing polymer with a terminal unsaturated carboxylate. This technology is well known to those skilled in the art. Compounds conform to the following structure;

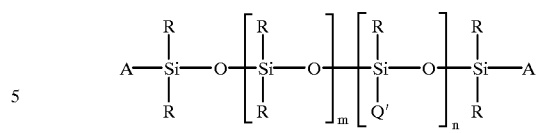

Wherein
R is methyl;
Q' is $(CH_2)_C$—C(O)—O—H:
c is an integer from 3 to 17;
A is methyl;
m is an integer ranging from 1 to 200;
n is an integer ranging 0 to 10 when A is —Q—$R^1$, and an integer ranging from 1 to 10 when A is R;

| Example | Name | c | n | m |
|---|---|---|---|---|
| 1 | Siltech C 1000 | 10 | 3 | 15 |
| 2 | Siltech C 1100 | 10 | 1 | 20 |
| 3 | Siltech C 1200 | 3 | 4 | 50 |
| 4 | Siltech C 1300 | 3 | 2 | 200 |
| 5 | Siltech C 1400 | 4 | 1 | 29 |
| 6 | Siltech C 1500 | 17 | 3 | 1 |
| 7 | Siltech C 1600 | 17 | 4 | 150 |
| 8 | Siltech C 1700 | 4 | 10 | 55 |

Terminal Substituted Carboxy Functional Silicone

Terminal substituted carboxy functional silicone compounds are well known and are marketed in the trade under many names.

The preferred method of placing this type of carboxyl group into the silicone polymer is by the reaction of terminal silanic hydrogen containing polymer with a terminal vinyl containing carboxy compound.

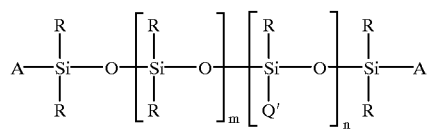

Wherein
R is methyl;
Q' is $(CH_2)_C$—C(O)—O—H;
c is an integer from 3 to 17;
n is 0;
A is —Q';

| Example | Name | c | m |
|---|---|---|---|
| 9 | Siltech CT 701 | 10 | 1 |
| 10 | Siltech CT 706 | 3 | 200 |
| 11 | Siltech CT 710 | 17 | 50 |
| 12 | Siltech CT 750 | 10 | 100 |
| 13 | Siltech CT 790 | 3 | 150 |

Compounds of the Present Invention
General Reaction Conditions

The esterification can be run without catalyst; however, when no catalysts used reaction rates are less efficient. Standard esterification catalysts are generally used at concentrations of between 0.05%, to 0.50% with a preferred range of 0.1% to 0.3%. Catalysts which are effective include but are not limited to; sulfuric acid, p-toluene sulfonic acid, methane sulfonic acid, tin metal, zinc metal, titanium metal, organo titianates, organo tin compounds, organo zinc compounds, zinc oxide, magnesium oxide, calcium oxide, etc. The most preferred catalyst is stannous oxylate. The reaction is conducted at between 140 and 240 C. under an inert nitrogen blanket. The nitrogen blanket preserves the color. Preferred temperature range is between 180 and 210 C. Water is removed from the reaction which is done using a nitrogen sparge or vacuum.

Examples 14–26

General Procedure

Into a suitable round bottom, three neck flask equipped with a Dean Stark trap, a thermometer and a nitrogen sparge is added the specified number of grams of the carboxy silicone (example 1–13) and the specified number of grams of sunscreening agent and 0.25% of total weight of the batch of catalyst. The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is used without additional purification.

Example 14

Into a suitable round bottom, three neck flask equipped with a Dean Stark trap, a thermometer and a nitrogen sparge is added the 609.0 grams of the carboxy silicone (Example 1), and 107.0 grams of benzophenone 1 and 0.25% of total weight of the batch of catalyst. The reaction mass is blanketed with nitrogen, and heated to 180 and 200 C. under an inert nitrogen blanket. Once the reaction temperature reaches 120 C. water begins to boil off and is collected in the Dean Stark Trap. Within four to five hours the theoretical water is collected off and the acid value is very low. The product is used without additional purification.

Example 15–26

Example 1 is repeated only this time substituting the specified number of grams of the specified carboxy silicone for the carboxy silicone specified and the number of grams of the specified benzophenone replacing benzophenone 1;
Note: In the below table Gms. is grams

| | Carboxy Silicone | | Sunscreening Agent | |
|---|---|---|---|---|
| | | Compound | Benzo- | |
| Example | Example | Grams | phenone | Grams |
| 15 | 2 | 1,827.0 | 3 | 228.0 |
| 16 | 3 | 1,051.0 | 3 | 228.0 |
| 17 | 4 | 7,570.0 | 4 | 308.0 |
| 18 | 5 | 2,409.0 | 6 | 137.0 |
| 19 | 6 | 361.0 | 8 | 122.0 |
| 20 | 7 | 3,100.0 | 10 | 242.0 |
| 21 | 8 | 524.0 | 12 | 326.0 |
| 22 | 9 | 290.0 | 1 | 242.0 |
| 23 | 10 | 7,553.0 | 3 | 228.0 |
| 24 | 11 | 2,200.0 | 4 | 308.0 |

| | Carboxy Silicone | | Sunscreening Agent | |
|---|---|---|---|---|
| | | Compound | Benzo- | |
| Example | Example | Grams | phenone | Grams |
| 25 | 12 | 4,000.0 | 6 | 137.0 |
| 26 | 13 | 5,700.0 | 8 | 122.0 |

Compounds of the present invention were found to have ultraviolet absorbtion spectra that were consistent with the sunscreens, that is both UV A and UV B. The compounds were found to be non-irritating to the skin and eyes. They form films on the skin and are comfortable and non-occlusive. When applied to fabrics, the fabrics do not yellow as rapidly when exposed to UV light.

The compounds of the present invention are good candidates for use in cosmetic products and in industrial applications were protection from UV is desired.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed:
1. A compound conforming to following structure:

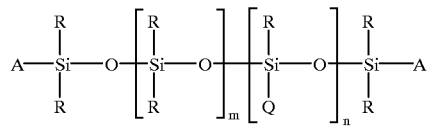

wherein:

R is methyl;

Q is a —$(CH_2)_C$—C(O)——$R^2$;

c is an integer ranging from 3 to 17;

A is selected from —R or —Q m is an integer ranging from 1 to 200;

n is an integer ranging 0 to 10 when A is —Q, and an integer ranging from 1 to 10 when A is R;

$R^2$ is selected from the group consisting of

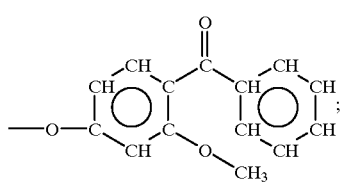

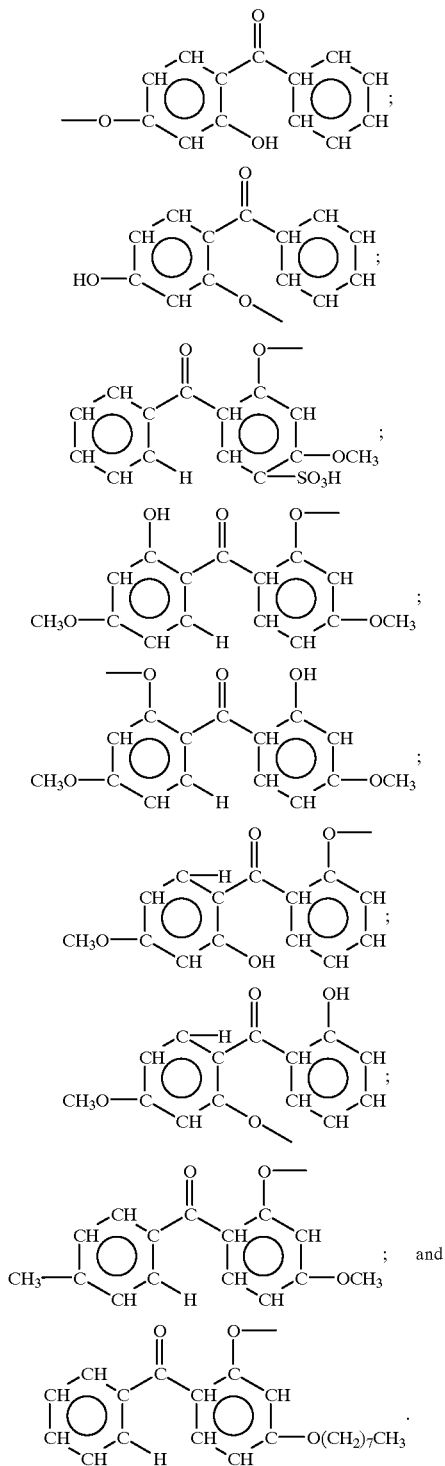
2. A compound of claim 1 wherein $R^2$ is
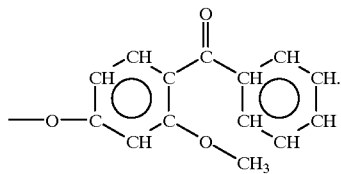
3. A compound of claim 1 wherein $R^2$ is
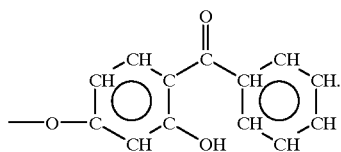
4. A compound of claim 1 wherein $R^2$ is
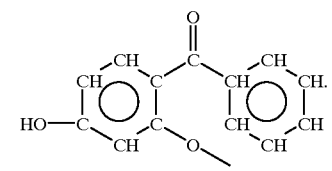
5. A compound of claim 1 wherein $R^2$ is
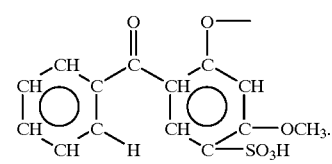
6. A compound of claim 1 wherein $R^2$ is
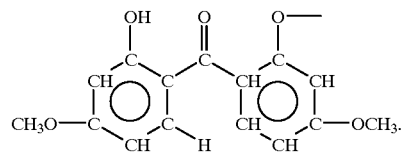
7. A compound of claim 1 wherein $R^2$ is
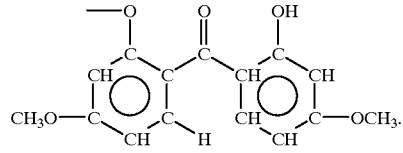

8. A compound of claim 1 wherein $R^2$ is
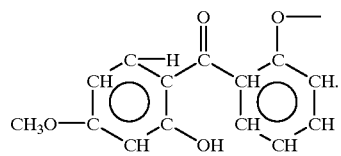
9. A compound of claim 1 wherein $R^2$ is
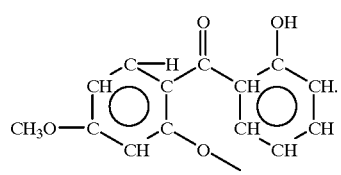
10. A compound of claim 1 wherein $R^2$ is
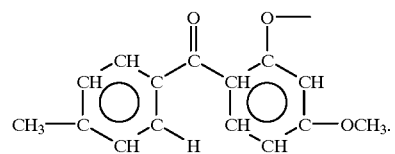
11. A compound of claim 1 wherein $R^2$ is
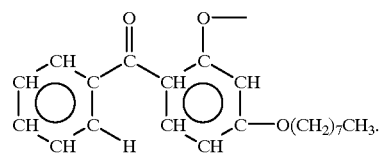
* * * * *